United States Patent
Shankle (10) Patent No.: US 8,412,664 B2
(45) Date of Patent: Apr. 2, 2013

(54) NON-NATURAL PATTERN IDENTIFICATION FOR COGNITIVE ASSESSMENT

(75) Inventor: William Rodman Shankle, Corona del Mar, CA (US)

(73) Assignee: Medical Care Corporation, Newport Beach, CA (US)

(*) Notice: Subject to any disclaimer, the term of this patent is extended or adjusted under 35 U.S.C. 154(b) by 315 days.

(21) Appl. No.: 12/922,451

(22) PCT Filed: Mar. 13, 2009

(86) PCT No.: PCT/US2009/037139
§ 371 (c)(1),
(2), (4) Date: Nov. 24, 2010

(87) PCT Pub. No.: WO2009/114795
PCT Pub. Date: Sep. 17, 2009

(65) Prior Publication Data
US 2011/0060715 A1    Mar. 10, 2011

Related U.S. Application Data

(60) Provisional application No. 61/036,881, filed on Mar. 14, 2008.

(51) Int. Cl.
*G06F 9/44* (2006.01)
*G06N 7/02* (2006.01)
*G06N 7/06* (2006.01)
*G09B 19/00* (2006.01)

(52) U.S. Cl. .......................................... 706/52; 434/236
(58) Field of Classification Search .................. 706/52; 434/236
See application file for complete search history.

(56) References Cited

U.S. PATENT DOCUMENTS

| 6,280,198 B1 | 8/2001 | Calhoun et al. |
| 2005/0102171 A1* | 5/2005 | Ashley et al. ............. 705/4 |
| 2005/0143630 A1 | 6/2005 | Darby et al. |

FOREIGN PATENT DOCUMENTS

| EP | 1139268 | 10/2001 |
| WO | 0205247 | 1/2002 |

OTHER PUBLICATIONS

Harpp, David and James Hogan "Crime in the CLassroom: Detection and prevention of cheating on multiple choice exams" 1993 [Online] Downloaded Nov. 26, 2012 http://pubs.acs.org/doi/abs/10.1021/ed070p306.*
Barclay, "Enhanced Recognition of Defectors Depends on Their Rarity," Cognition, 2008, 107, pp. 817-828, 12 pages.

(Continued)

*Primary Examiner* — Ben Rifkin
(74) *Attorney, Agent, or Firm* — Fish & Richardson P.C.

(57) ABSTRACT

Methods, systems, and apparatus, including medium-encoded computer program products, for detection of cheating on a cognitive test. In one aspect, a method includes receiving first information concerning a person, the first information specifying the person's responses, and lack thereof, for items of a cognitive test administered to the person, wherein the cognitive test includes multiple item-recall trials used to assess cognitive impairment; analyzing the first information using a classification algorithm trained on second information concerning a group of people to whom the cognitive test has been administered, the classification algorithm generated in accordance with a first part and a second part, the first part distinguishing between cheaters and non-cheaters, and the second part distinguishing between impaired cheaters and non-impaired cheaters; and identifying, based on the analyzing, the person as a cheater requiring a verification test to confirm an initial result of the cognitive test.

20 Claims, 5 Drawing Sheets

OTHER PUBLICATIONS

Buyse et al., "The Role of Biostatistics in the Prevention, Detection and Treatment of Fraud in Clinical Trials," Statistics in Medicine, 1999, vol. 18, pp. 3435-3451, 17 pages.

Cho, et al., "Early Detection and Diagnosis of MCI Using the MCI Screen Test," The Japanese Journal of Clinical and Experimental Medicine, 2007; 84(8), pp. 1152-1160, 9 pages.

da Rocha et al., "Cheating on College Examinations," Psychological Reports, 2007, 100, pp. 379-386, 8 pages.

Fu et al., "Lying in the Name of the Collective Good: a Developmental Study," Developmental Science, 2008, 11(4), pp. 495-503, 9 pages.

Lippi et al., "New Strategies for Doping Control," Journal of Sports Sciences, Mar. 2008, 26(5), pp. 441-445, 5 pages.

McManus et al., "Learning in Practice—Detecting cheating in written medical examinations by statistical analysis of similarity of answers: pilot study," BMJ, May 7, 2005, vol. 330, pp. 1064-1066, 3 pages.

Muhney, Kelly A. et al., "The Prevalence of Academic Dishonesty in Texas Dental Hygiene Programs," Journal of Dental Education, Nov. 2008, pp. 1247-1260, 14 pages.

Oda et al., "Does an Altruist-Detection Cognitive Mechanism Function Independently of a Cheater-Detection Cognitive Mechanism? Studies using Wason selection tasks," Evolution and Human Behavior, Mar. 2006, 27, pp. 366-380, 15 pages.

Powrie et al., "Detection of Growth Hormone Abuse in Sport," Growth Hormone & IGF Research, 2007, 17, pp. 220-226, 7 pages.

Rubin et al., "Children's Verbalizations and Cheating Behavior During Game Playing: The Role of Sociometric Status, Aggression, and Gender," Journal of Abnormal Child Psychology, Feb. 2003, 31(1), pp. 65-78, 14 pages.

Russano et al., "Investigating True and False Confessions Within a Novel Experimental Paradigm," American Psychological Society, 2005, 16(6), pp. 481-486, 6 pages.

Shankle et al., "Method to improve the detection of mild cognitive impairment", PNAS, Mar. 2005, vol. 102, No. 13, pp. 4919-4924, 6 pages.

Trenkle, et al., "Detecting Cognitive Impairment in Primary Care: Performance Assessment of Three Screening Instruments," Journal of Alzheimer's Disease, Jun. 2007, 11(3), pp. 323-335, 13 pages.

* cited by examiner

NON-NATURAL PATTERN IDENTIFICATION FOR COGNITIVE ASSESSMENT

CROSS REFERENCE TO RELATED APPLICATIONS

This application claims the benefit of the priority of U.S. Provisional Application Ser. No. 61/036,881, filed Mar. 14, 2008 and entitled "Non-Natural Pattern Identification During Cognitive Assessment".

BACKGROUND

This specification relates to assessing the cognitive function of a person to whom a cognitive test has been administered, and in particular to detection of cheating on a cognitive test.

Various techniques have been used to measure the cognitive function of a person. For example, the National Institute of Aging's Consortium to Establish a Registry of Alzheimer's Disease (CERAD) has developed a ten word list as part of the Consortium's neuropsychological battery. The CERAD word list (CWL) test consists of three immediate-recall trials of a ten word list, followed by an interference task lasting several minutes, and then a delayed-recall trial, with or without a delayed-cued-recall trial. The CWL is usually scored by recording the number of words recalled in each of the four trials. A single cutoff score for the delayed-recall trial, with or without adjustment for demographic variables, is typically used to determine whether cognitive impairment exists.

Some have proposed various improvements to the CWL. In addition, the CWL and the improvements thereof have been used to provide memory performance testing services, via the Internet, to clinicians in daily practice. Such services allow rapid testing of individual patients and reporting on the results of such testing. Previous reports for individual cognitive performance test results have included a statement of whether the patient has been found to be normal or to have cognitive impairment.

Furthermore, in the long-term care insurance industry, individuals applying for a policy must typically be determined to not have cognitive impairment or dementia due to Alzheimer's disease or a related disorder (ADRD). Insuring such an impaired individual can result in a typical claims cost of more than $200,000 per case, assuming four years of claims payments. The insurer therefore wishes to avoid insuring applicants who already have ADRD. For this reason, insurers pay underwriters to administer cognitive testing that is both sensitive to detect mild cognitive impairment, as well as specific to correctly identify normal aging. To reduce the costs of such cognitive testing, insurers are increasingly testing applicants over the telephone.

SUMMARY

This specification describes technologies relating to assessing the cognitive function of a person to whom a cognitive test has been administered, and in particular to detection of cheating on a cognitive test.

In general, an aspect of the subject matter described in this specification can be embodied in one or more methods that include receiving first information concerning a person, the first information specifying the person's responses, and lack thereof, for items of a cognitive test administered to the person, wherein the cognitive test includes multiple item-recall trials used to assess cognitive impairment; analyzing the first information using a classification algorithm trained on second information concerning a group of people to whom the cognitive test has been administered, the classification algorithm generated in accordance with a first part and a second part, the first part distinguishing between cheaters and non-cheaters, and the second part distinguishing between impaired cheaters and non-impaired cheaters; and identifying, based on the analyzing, the person as a cheater requiring a verification test to confirm an initial result of the cognitive test. Other embodiments of this aspect include corresponding systems, apparatus, and computer-readable media encoding computer program product(s) operable to cause data processing apparatus to perform the operations.

These and other embodiments can optionally include one or more of the following features. The classification algorithm can be configured to check for cheating strategies characteristic of persons with Alzheimer's disease or a related disorder (ADRD). The classification algorithm can be selected to maximize sensitivity while minimizing reduction in specificity, which preserves a high negative predictive value while maintaining a low misclassification rate for impaired cheaters. Moreover, the group of people can include a first sample and a second sample, where the method further includes: analyzing data in the first part for the first sample to identify a subset of variables that discriminate between cheaters and non-cheaters, and validating results in the first part using the second sample; and analyzing, in the second part, data of persons identified as cheaters in the first part to identify a subset of variables that discriminate between impaired cheaters and non-impaired cheaters.

The subset of variables that discriminate between cheaters and non-cheaters can include education and multiple numbers corresponding to items recalled on two or more of the multiple item-recall trials including a delayed free recall trial, and the subset of variables that discriminate between impaired cheaters and non-impaired cheaters can include age, gender, education and a number corresponding to items recalled on at least one of the multiple item-recall trials. The multiple item-recall trials can include word recall tests of memory, and the analyzing can include distinguishing between impaired and non-impaired individuals based on a total number of words recalled across the trials. The analyzing can include evaluating a probability of an order of items recalled by the person given probabilities of recall patterns for the group of people.

A system can include a user device; and one or more computers operable to interact with the device and to perform operations including those of the method discussed above. The one or more computers can include a server system operable to interact with the device through a data communication network, and the device can be operable to interact with the server as a client. Moreover, the device can include a user interface device, the one or more computers can include the user interface device, and the operations can further include outputting an indication of the identified person to a device including a computer-readable medium.

Particular embodiments of the subject matter described in this specification can be implemented to realize one or more of the following advantages. Cheaters can be readily detected from information specifying answers on a cognitive test that includes multiple item-recall trials used to assess cognitive impairment. Analysis of the word order across multiple item-recall trials can significantly increase the ability to detect cheaters. Moreover, substantial savings can be realized by detecting 1) test cheaters so as to avoid inappropriate insurance policies being issued; 2) cheating by insured individuals attempting to fail a test to obtain long-term care insurance claims benefits early; 3) cheating by individuals attempting to do worse on a test to become eligible for a clinical trial; and 4) cheating by professionals attempting to pass a cognitive test that is required for their continued employment.

Moreover, the systems and techniques described can be implemented for use in other scenarios in which individuals are tested on their cognitive abilities. Examples include taking entrance exam tests for admission to professional schools, taking tests to qualify for a benefit, an insurance policy or a clinical drug trial, and competitions for prizes, prestige or recognition by others, or other scenarios where individuals have an incentive to do well on a given test.

The details of one or more embodiments of the subject matter described in this specification are set forth in the accompanying drawings and the description below. Other features, aspects, and advantages of the invention will become apparent from the description, the drawings, and the claims.

DETAILED DESCRIPTION

Figure 1:
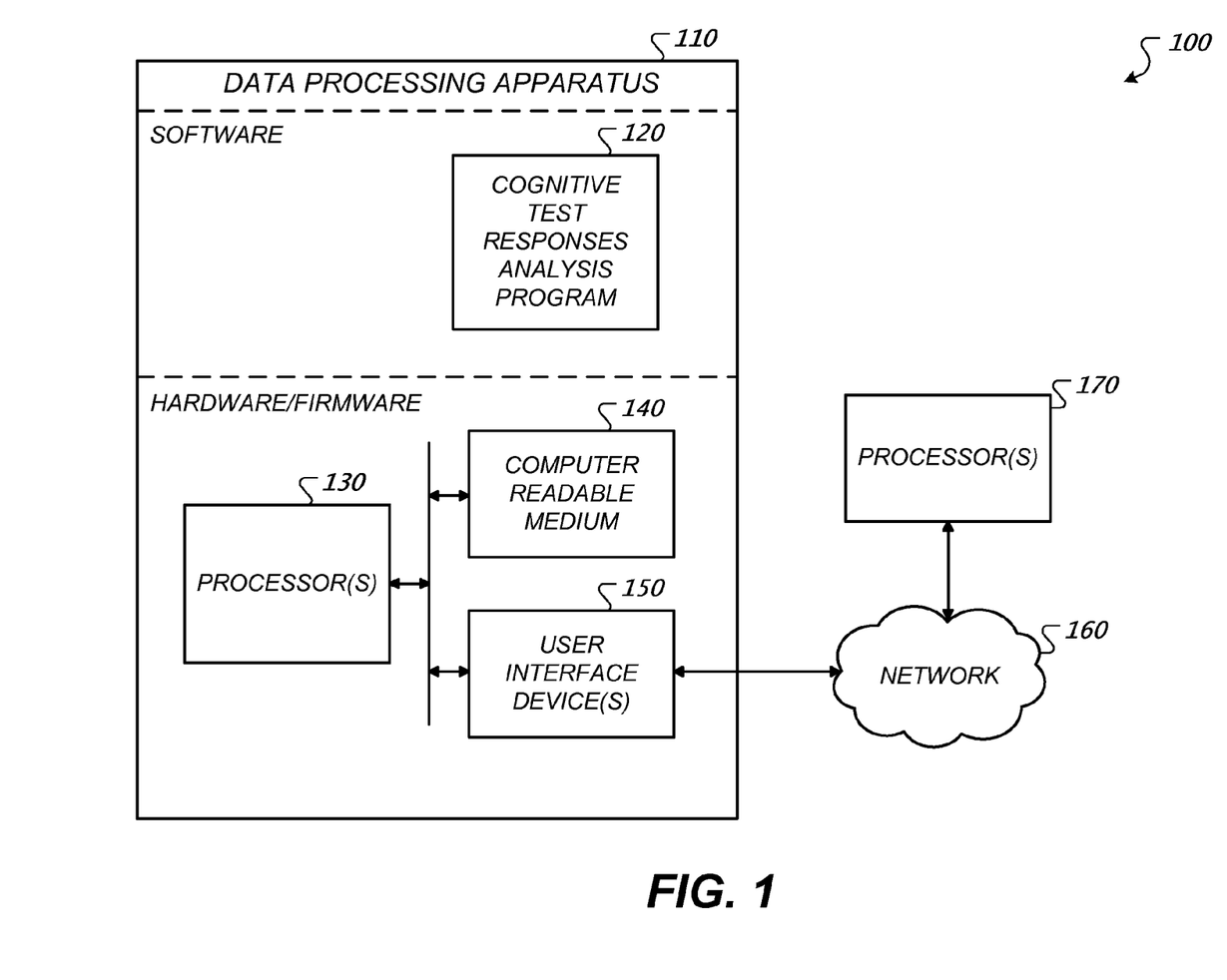
FIG. 1 shows an exemplary system used to identify cheaters on a cognitive test.

FIG. 1 shows an exemplary system 100 used to identify cheaters on a cognitive test. A data processing apparatus 110 can include hardware/firmware and one or more software programs, including a cognitive test responses analysis program 120. The cognitive test responses analysis program 120 operates in conjunction with the data processing apparatus 110 to effect various operations described in this specification. The program 120, in combination with the various hardware, firmware, and software components of the data processing apparatus, represents one or more structural components in the system, in which the algorithms described herein can be embodied.

The program 120 can be an application for performing analysis on data collected to assess the cognitive function of a subject. An application refers to a computer program that the user perceives as a distinct computer tool used for a defined purpose. An application can be built entirely into an operating system or other operating environment, or it can have different components in different locations (e.g., a remote server). The program 120 can include or interface with other software such as database software, testing administration software, data analysis/computational software, and user interface software, to name a few examples. For example, the program 120 can include or interface with software that collects data and analyzes the cognitive function or otherwise assesses the brain condition of a person.

Interface software can also be included that operates over a network to interface with other processor(s), such as in a computer used by a test taker or test administrator. For example, the program 120 can include software methods for inputting and retrieving data associated with a cognitive assessment test, such as score results, or demographic data. Such a cognitive assessment test can be administered using the program 120, or the program 120 can be used to collect and analyze data from a cognitive assessment test administered in another manner, such as an in-person or a test administered by telephone. In addition, the program 120 can also effect various analytic processes, which are described further below.

The data processing apparatus includes one or more processors 130 and at least one computer-readable medium 140 (e.g., random access memory, storage device, etc.). The data processing apparatus 110 can also include one or more user interface devices 150. User interface devices can include display screen(s), keyboard(s), a mouse, stylus, modems or other networking hardware/firmware, or any combination thereof to name a few examples. The subject matter described in this specification can also be used in conjunction with other input/output devices, such as a printer or scanner. The user interface device can be used to connect to a network 160, and can furthermore connect to a processor or processors 170 via the network 160 (e.g., the Internet).

Therefore, a user of the analysis program 120 does not need to be local, and may be connecting using a web browser on a personal computer, or using other suitable hardware and software at a remote location. For example, a clinician at a testing center can access a web interface via the remote processor 170 in order to input test data for a cognitive test. The test data can be the results of an already administered test, or the test data can be the information exchanged when actually administering the cognitive test using a network based testing system. In any event, data can be transmitted over the network 160 to/from the data processing apparatus 110. Furthermore the clinician can input test data and retrieve analysis based on that data or other data stored in a database. Note that the data processing apparatus 110 can itself be considered a user interface device (e.g., when the program 120 is delivered by processor(s) 170 as a web service).

The system 100 can be used to analyze data from various types of cognitive function or brain condition assessment tests. The following description provides extensive details with respect to detecting test cheaters in the context of persons with Alzheimer's disease or a related disorder (ADRD). However, the systems and techniques described can be implemented for use in other scenarios in which individuals are tested on their cognitive abilities. Thus, the systems and techniques described can be used in many different contexts to detect cheating among persons taking neuropsychologic tests.

In the context of ADRD, if an individual already has ADRD, they have a strong incentive to try and obtain a long-term care insurance policy to cover the costs of their care. If they take the test over the telephone, it is easy to cheat by taking notes on what items they will be asked to recall later. Such cheating could result in an ADRD individual being issued a long-term care insurance policy that will cost the insurer upwards of $200,000.

Because of the increased use of telephone testing when applying for a long-term care insurance policy, more individuals already affected by ADRD will be able to cheat and pass the test to receive a long-term care insurance policy. Based on results discussed below, it is estimated that of 100,000 applicants for long-term care insurance annually tested by telephone, approximately 1,140 individuals with ADRD will cheat and pass testing to receive a policy. This can result in annual claims costs of around $228 million or more to the long-term care insurance industry. It is therefore advantageous for insurers to devise strategies to detect cheating when applicants are tested by telephone.

The strategies that people use to cheat on a cognitive test are limited. In the case of cheating by the test taker, cheating fundamentally involves the use of a strategy of providing answers without an examiner realizing that the person being tested is obtaining them in violation of the rules of the test. For example, in testing memory over the telephone, a person may write down all the words they are asked to remember and recall later. When asked to recall the words, they may then read the list back to the examiner. The way that the person reads the words back to the examiner constitutes their cheating strategy. One person's cheating strategy may be to read back the words in the order they were presented. Another's cheating strategy may be to read back the words in their reverse order. Another's cheating strategy may be to read back the list of words in a random order.

In deciding whether a person is cheating, one can compare their memory performance to well characterized patterns observed among non-cheating individuals. These normal patterns of memory retrieval are non-intuitive and quite distinct from most cheating strategies conjured up by individuals. These normal patterns of memory performance consist of (1) changes in total numbers of words recalled across successive learning and testing trials, and (2) stereotypical orderings of the words recalled in each trial.

Figure 2:
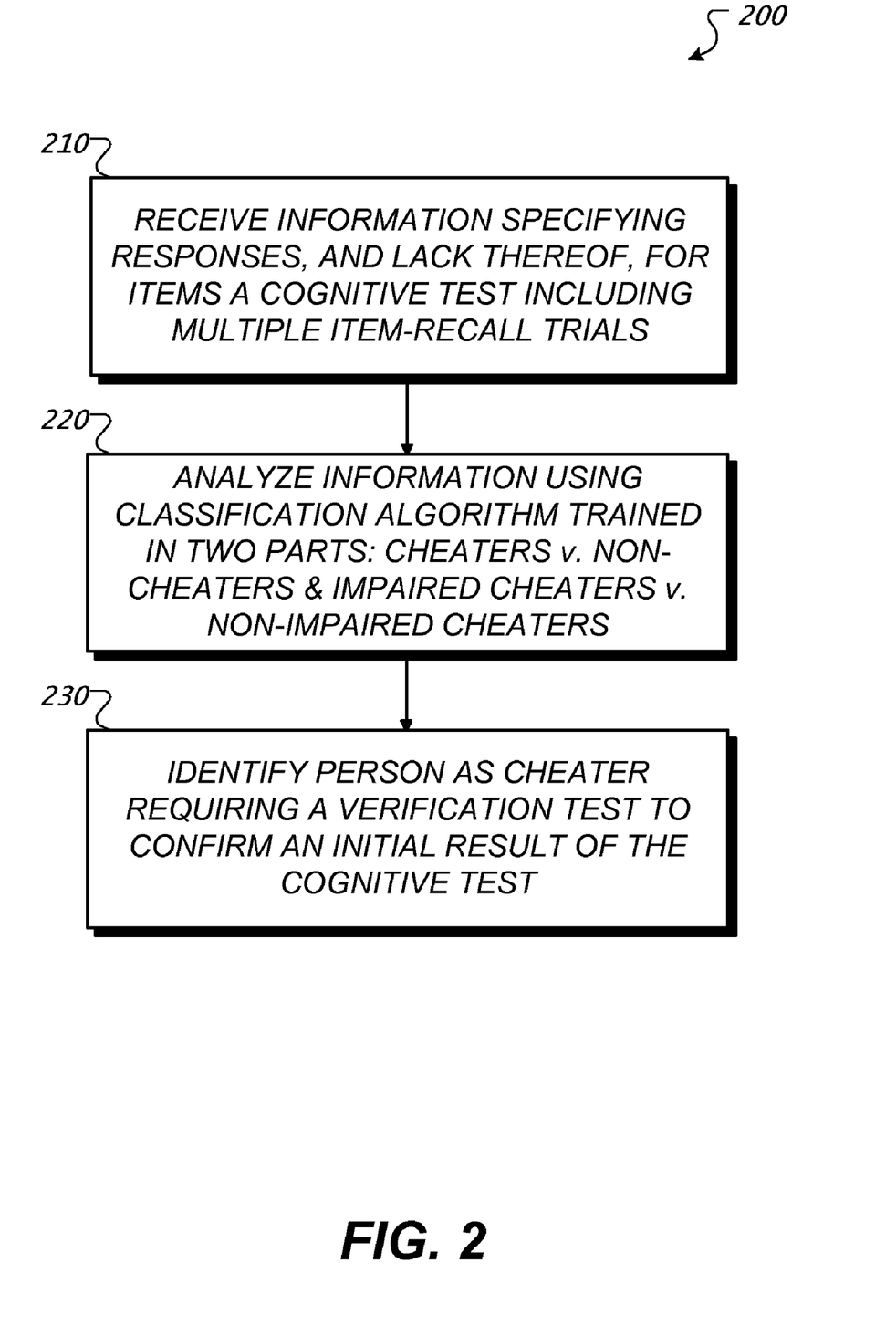
FIG. 2 shows an exemplary process used to identify cheaters on a cognitive test.

FIG. 2 shows an exemplary process 200 used to identify cheaters on a cognitive test. First information is received (210) concerning a person, where the first information specifies the person's responses, and lack thereof, for items of a cognitive test administered to the person. The information can be from a previously administered test or from a test that is currently being administered. Nonetheless, the exemplary process described in connection with FIG. 2, and other implementations of the more general concepts underlying this exemplary process, are not practiced on the human body since such processes do not themselves involve an interaction necessitating the presence of the person.

The test can be administered in-person, over the phone, through a computer network (e.g., through the Web over the Internet), or in another manner Note that for in-person administration of the test, the present system and techniques can still provide benefits in that cheating can be detected in the event that the test administrator is in collusion with the test taker or the test administrator is not sufficiently trained to accurately detect cheating that occurs during an in-person administration of the cognitive test.

The cognitive test can include multiple item-recall trials, which can further include at least one item common to a subset of the recall trials, the subset including at least two of the recall trials. Alternatively, the multiple item-recall trials can have no items in common. In general, the full set of information in the test should be recorded, including all components of the test and all subject responses. The information can be received (210) from a database, a network or web-enabled device, a computer readable medium, or a standard input output device on a computer system, to name just a few examples. The cognitive test can include a test of attention and recall, and the test components can include items (e.g., words) to be recalled in one or more trials. For example, a test of attention and recall can include the CERAD word list (CWL) and/or other lists of words or items.

The CWL is a test of immediate and delayed free recall and delayed cued recall that was developed by the National Institute of Aging CERAD centers in the 1980s. There are three learning trials in which the subject is presented each word in the list and repeats it, then at the end of the list, recalls as many words as they can. The subject is not instructed to recall the words in the order they are presented, but rather to recall as many words as they can immediately after being presented the list of ten words. They are also instructed that a few minutes after the third learning trial they will again be asked to recall as many of the words as they can without another presentation of the words. The words are presented in a different order for each learning trial. The number of words correctly recalled is recorded for each of the three learning trials. After the third learning trial, an interference task that distracts the subject from rehearsing the word list (e.g., a test of executive function, which can consist of the subject being asked to select which of three animals is most different from the other two, and is given 12 such triads of animals to make decisions upon) is given over a period of two to five minutes. After the interference task, the subject is asked to recall as many of the ten words as they can (delayed free recall trial). The number of words correctly recalled is recorded. After the delayed free recall trial, the subject is given a delayed recognition task. The subject is presented the ten CWL words intermixed with ten distracter words. For each word, the subject is asked whether it was one of the CWL words, and the subject's response (yes or no) is recorded.

Since the words of the trials are already known, the first information need not specify the words themselves, but rather just whether or not a given word was recalled. For example, eight word lists can be used, with each word list including ten words for learning and recall, plus ten more words for delayed-cued-recall. Four trials can be employed in the cognitive test, where one of the eight word lists can be selected for use in the test. The first set of ten words from the list can be used in the immediate and delayed free recall trials (and the words of the list can be presented in the same order in each trial or in a different order), and the second set of ten words can be used as the distracter word list for the delayed-cued-recall trial. The first information can include an eighty column binary score (i.e., an eighty bit vector) that corresponds to the responses received on the immediate and delayed free recall trials of the cognitive test. Each bit in this example indicates whether a corresponding word from a trial was recalled, or whether the corresponding word from the trial was not recalled.

For example, an eighty columns wide binary indicator matrix can be defined as follows. Each word in each trial can occupy 2 columns. The first column can be assigned a 1 if the word in the trial was recalled and a 0 if it was not recalled. The second column can be assigned a 0 if the word in the trial was recalled and a 1 if it was not recalled. Each trial with ten words thus occupies twenty columns for a total of eighty columns for the four free recall trials of the word list trials. With this arrangement, the binary indicator matrix gives a row total of forty, which permits the determination of an optimal column score for a word when it was recalled in a trial, as well as a different optimal column score when that word was not recalled in a trial.

The words in each word list can be linguistically and statistically equivalent. The words on each distinct list can have the same level of intra-list associability and usage frequency. Each list of words can have the same level of associability and usage frequency with each and every other list of words. For example, the eight word lists used can be as shown in Table 1:

TABLE 1

Word Lists

|     | List 1    | List 2    | List 3    | List 4    | List 5     | List 6   | List 7   | List 8  |
|-----|-----------|-----------|-----------|-----------|------------|----------|----------|---------|
| W1  | BUTTER    | BEDROOM   | CAKE      | CLOCK     | BIBLE      | OAK      | JAZZ     | BAT     |
| W2  | ARM       | DOWN      | PARK      | SCALE     | FEMALE     | RANK     | BUS      | SAFETY  |
| W3  | SHORE     | MESSAGE   | WISDOM    | THREAT    | LEGEND     | TASTE    | LID      | COPY    |
| W4  | LETTER    | BIRTHDAY  | MARRIAGE  | SPORT     | STAMP      | SPRING   | CRITIC   | ROOF    |
| W5  | QUEEN     | WIND      | REST      | SPACE     | TOOTH      | BRAND    | DARK     | ACTOR   |
| W6  | CABIN     | TRUCK     | NOTICE    | LAYER     | FAT        | PROJECT  | OWNER    | VISIT   |
| W7  | POLE      | LEADER    | BOAT      | AMOUNT    | GLOVE      | SERVANT  | GUEST    | POOL    |
| W8  | TICKET    | HAT       | PLANET    | FLOOD     | LECTURE    | CUP      | WEATHER  | GRIEF   |
| W9  | GRASS     | BARN      | KNEE      | DOUBLE    | BEAST      | LIST     | PEACE    | SLEEVE  |
| W10 | ENGINE    | SOCK      | TELEPHONE | RESPECT   | AGENT      | PLAIN    | BASE     | OUTCOME |
| D1  | CHURCH    | WINTER    | BLANKET   | TOUCH     | SHOW       | CAMP     | MUSCLE   | DANCE   |
| D2  | COFFEE    | BAG       | VEIN      | FLOOR     | CASH       | BATHROOM | ORGAN    | REGION  |
| D3  | DOLLAR    | BLUE      | SHAPE     | LEATHER   | HELICOPTER | OIL      | WEDDING  | SMOKE   |
| D4  | FIVE      | ROOT      | NEWSPAPER | ARROW     | FLOWER     | EARTH    | WOOD     | BLADE   |
| D5  | HOTEL     | TRAIL     | MISSION   | KID       | NUT        | BEEF     | SUPPORT  | STRESS  |
| D6  | MOUNTAIN  | SEED      | WATCH     | BUCKET    | SILVER     | LUNCH    | PARKING  | LIMIT   |
| D7  | SLIPPER   | HEART     | LIGHT     | CONFLICT  | BOTTLE     | PORTRAIT | BRANCH   | TRIAL   |
| D8  | VILLAGE   | SOUP      | PINT      | DUST      | LOYALTY    | HOST     | PHOTO    | PENCIL  |
| D9  | STRING    | NOISE     | CYCLE     | PRESSURE  | LOAD       | STRUGGLE | VERSE    | WIFE    |
| D10 | TROOP     | CREATURE  | MOUTH     | SPELL     | DECADE     | RIDE     | LOUNGE   | PLAYER  |

W#: 10 Word List used in learning trial to be recalled
D#: Used in Delayed-Cued-Recall Trial along with the 10 Word List The word lists can be used in different parts of a test (e.g., the distracter and learning word lists can be interchanged). Moreover, the words in each word list can be presented in the same order or different order. For example, a shuffled order can be employed over multiple trials, such as in the CERAD or the ADAS-Cog (Alzheimer's Disease Assessment Scale-cognitive subscale) cognitive assessment tools. ADAS-cog consists of eleven tasks measuring different cognitive functions. The ADAS-Cog word recall test has the same general method of test administration as the CWL. Note that the ADAS-Cog but does not use the 10-word list for cued recall that is used in the immediate and delayed free recall trials. It has its own set of words for that.

In general, the words in each word list should have the same difficulty of being recalled as the other words on that list, as well as the words in the other lists. For each learning trial, the words can be presented in the same order or in different order. It will be appreciated that other data formatting approaches, as well as other cognitive tests and test components, are also possible.

Other cognitive assessment tests can include, but are not limited to other multiple word recall trials, other recall or cued recall tests of verbal or non-verbal stimuli, tests of executive function, including triadic comparisons of items, (e.g., deciding which one of three animals is most different from the other two), tests of judgment, similarities, differences or abstract reasoning, tests that measure the ability to shift between sets or perform complex motor sequences, tests that measure planning and organizational skill, tests of simple or complex motor speed, tests of language abilities including naming, fluency or comprehension, tests of visual-perceptual abilities including object recognition and constructional praxis. In one implementation, subjects are asked to recall the nine animals that were used for the triadic comparisons interference task that was given between the third learning trial and the delayed free recall trial. This delayed free recall of animals differs from that of the wordlist in that the subject is not asked to remember the animal names to recall them later, and therefore may not write them down if they are cheating. Differences between the delayed free recall of the animals and of the wordlist can help identify test cheaters. Examples of recorded data can include the words recalled, the words not recalled, the order of the words recalled, time delay before recall, the order in which intrusions and repetitions are recalled, and various aspects of test performance. Moreover, the cognitive test can include one or more trials performed to determine specific cognitive functions such as physical (e.g. orientation or hand-eye coordination) or perception based tests. Additional information can be obtained in order to classify the score, such as demographic information, or the date(s) of test administration, to name just two examples.

In any case, the first information is analyzed (220) using a classification algorithm trained on second information concerning a group of people to whom the cognitive test has been administered. The classification algorithm is generated in accordance with a first part and a second part, where the first part distinguishes between cheaters and non-cheaters, and the second part distinguishes between impaired cheaters and non-impaired cheaters. Thus, the classification algorithm characterizes the ability to detect cheating among normal and impaired individuals (e.g., those with ADRD). In the context of multiple item-recall trials, this can be done based on the total numbers of words recalled across trials (e.g., the total scores of the various trials of the CERAD wordlist), upon ratios of total scores for different pairs of trials, upon the recall of a given word or set of words across trials, upon the order in which a given word or set of words is recalled across trials, or based upon the orderings of words recalled per trial to detect different types of cheaters.

The classification algorithm can be configured to check for cheating strategies characteristic of normal persons and persons with some impairment, such as ADRD. One reason to think that individuals impaired with ADRD may have a different cheating strategy than normal individuals is that executive function is affected early in ADRD. Individuals use executive function to select a cheating strategy. The cheating strategy for impaired ADRD individuals may therefore be simpler or differ in some other way than that for normal individuals. Identification of a subset of cheating strategies that characterize most impaired ADRD individuals (or individuals with other executive function impairments) can improve the accuracy of cheating detection and reduce the costs required to re-test suspected cheaters in a setting where they cannot cheat.

The person can thus be identified (230), based on the analyzing (220), as a cheater requiring a verification test to confirm an initial result of the cognitive test. The verification test can be the same cognitive test administered using a different protocol. For example, when the test is initially administered by phone, the verification test can be an in-person or video-monitored administration of the same cognitive test with a different set of similar stimuli, such as a different, but equivalent, wordlist. Alternatively, the verification test can be a different test than the initially administered cognitive test. For example, if the test is initially administered by phone, the verification test could consist of a second test administered by phone in which the stimuli, such as tones, cannot be written down.

Figure 3A:
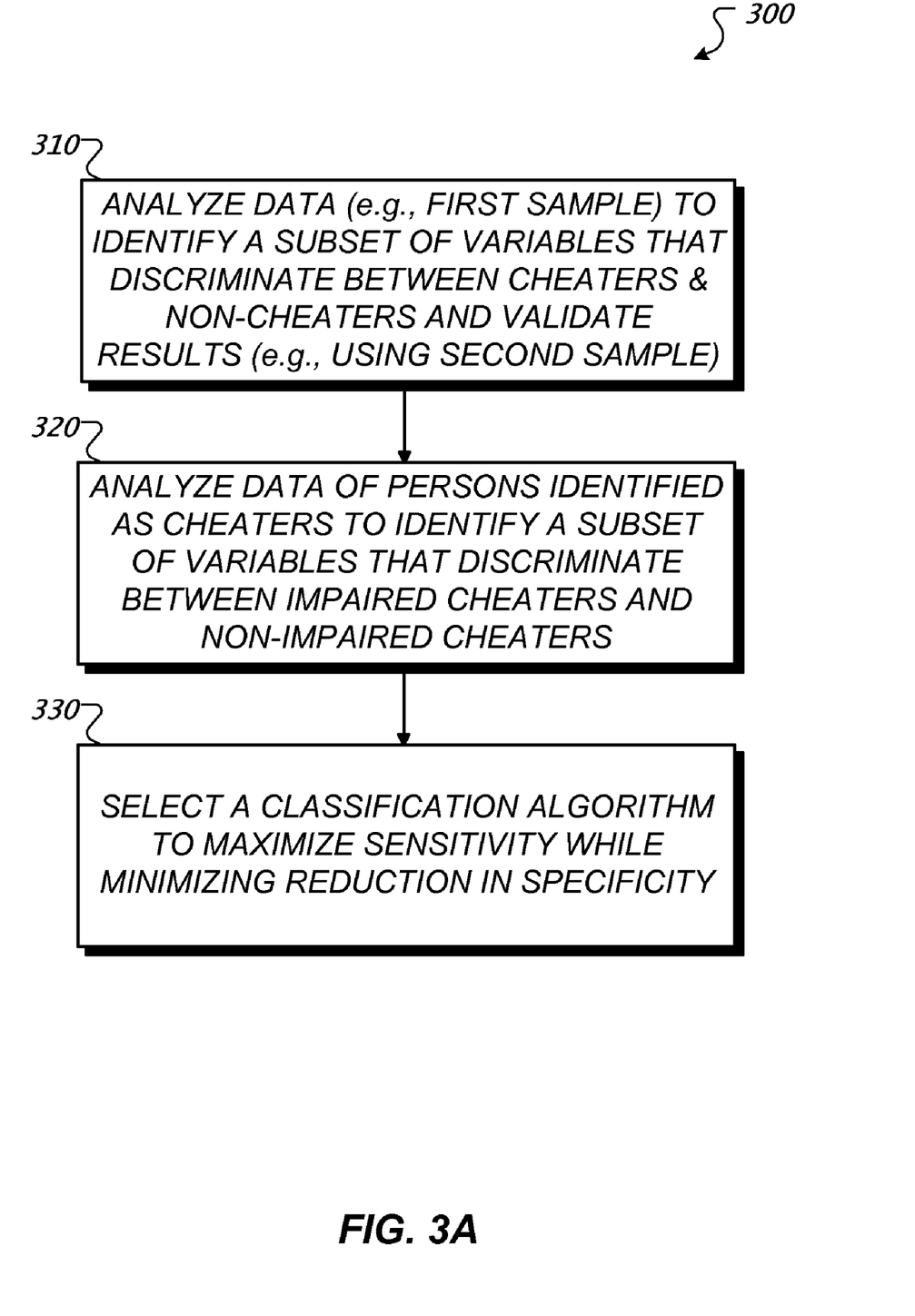
FIG. 3A shows an exemplary process of generating a classification algorithm to identify cheaters on a cognitive test.

FIG. 3A shows an exemplary process 300 of generating a classification algorithm to identify cheaters on a cognitive test. In a first part of algorithm generation, data can be analyzed to identify a subset of variables that discriminate between cheaters and non-cheaters, and results in the first part can be validated (310). The group of people used to train the classification algorithm can include a first sample and a second sample, the data analyzed in the first part can come from the first and second samples, and the results in the first part can be validated using a different mixture of the second sample, such as described in further detail below.

In a second part of algorithm generation, data of persons identified as cheaters in the first part can be analyzed to identify a subset of variables that discriminate between impaired cheaters and non-impaired cheaters (320). The persons identified as cheaters can be from the second sample, the first sample, or both. The analysis operations (310, 320) can be performed multiple times using different inputs to create multiple variations of the classification algorithm. In any case, a classification algorithm can be selected to maximize sensitivity while minimizing reduction in specificity, which preserves a high negative predictive value while maintaining a low misclassification rate for impaired cheaters (330).

A detailed example is now discussed, in which total scores as well as ratios of total scores of the various sub-tests of a memory test were examined. In this example, the first sample included 50 subjects with no evidence of cognitive impairment and normal job performance who were administered a memory test over the telephone twice. In this example, the subjects in the first sample were assigned at random to cheat on either the first or the second test, and instructed to not cheat on the other test. Moreover, the subjects did not receive the same wordlist for the two tests.

The second sample included 15,467 individuals applying for long-term care insurance who took the memory test over the telephone and passed the test. They were asked at the end of the test whether they had written down any words. If they answered yes, they were classified as reported cheaters. They were also evaluated for suspected cheating based on pre-established criteria, such as a highly suspicious pattern of words recalled. Applicants suspected of cheating were classified as suspected cheaters. Of these 15,467 individuals, 15,038 had complete data that allowed for full analysis. The sample was therefore restricted to the 15,038 applicants with complete data.

A 30% sub-sample of the suspected and reported cheaters were administered the test a second time (N=847). This time, they were administered the test in-person to prevent cheating. Those applicants who failed the in-person test were classified as impaired cheaters, while those who passed were classified as unimpaired cheaters.

Candidate Variables For Cheating Classification Algorithm—Candidate variables that were examined to detect cheaters in parts 1 and 2 of the cheating algorithm included demographics (age, gender, education) and variables assessing different aspects of the individual's cognitive test performance. These cognitive variables included total numbers of words recalled on each of the trials, the 6 ratios of the total numbers of words recalled for all possible pairs of four trials, the numbers of words recalled that were repetitions or intrusions (words not in the list) in each trial, the delayed free recall of animals (a separate measure of memory performance in which there was no specific instruction to try and remember, later on, the 9 animals that are presented to the subject—three at a time—as they are asked to select which animal is most different from the other two), and the ratio of the number of words recalled on the delayed free recall from the 10-word list compared to the delayed free recall of the 9 animals from the triadic comparisons task.

Cheating Algorithm Part 1—Cheaters Versus Non-Cheaters: The training sample had 208 subjects and consisted of all sample 1 subjects plus an equal number of sample 2 cheater and non-cheater subjects. Stepwise logistic regression was then performed on the candidate variables to remove ones that were clearly non-predictive. For the remaining variables, a bootstrap procedure was then applied, in which two thirds of the cheaters and two thirds of the non-cheaters in the training sample were randomly selected one thousand times, and logistic regression was performed each time. These thousand runs generated bootstrapped confidence intervals of the coefficient values for each of the remaining candidate variables. Any candidate variable whose bootstrapped confidence interval included zero was removed from the classification model. Variables included in the final part 1 model discriminating cheaters from non-cheaters included education, the number of words recalled on the first learning trial and on the delayed free recall trial, the ratio of the numbers of words recalled on trial 2 versus trial 1, the ratio of the corresponding numbers for the delayed free recall trial versus learning trial 2, and the ratio of the number of words recalled on delayed free recall of the wordlist versus that of the animals. Additional parameters that properly weighted the classification algorithm of cheater versus non-cheater included the prior probability of cheating by applicants for long-term care policies in the absence of other knowledge.

To validate the final part 1 algorithm, the set of the 847 sample 2 subjects were classified using the algorithm, and a non-parametric receiver operating characteristic (ROC) curve was used to estimate overall accuracy. The ROC curve defines the overall accuracy as the area under the curve, and defines the possible pairs of sensitivity and specificity values for discriminating cheaters from non-cheaters as points on the curve (regardless of whether the cheaters were normal or impaired). Applicants from sample 2 who were classified as cheaters were then submitted to part 2 of the algorithm to discriminate non-impaired cheaters from impaired cheaters.

The algorithm for part 1, which is applied to persons who had taken the cognitive test by telephone and were classified as normal, was as follows: $Y=-\ln[\beta_0*(\text{prevalence of not cheating})]+\beta_1*\text{education}+\beta_2*\text{Trial 1 Total}+\beta_3*\text{Delayed Free Recall Trial Total}+\beta_4*(\text{Trial 2 Total/Trial 1 Total})+\beta_5*(\text{Delayed Free Recall Trial Total/Trial 2 Total})+\beta_6*\text{Delayed Free Recall Of Animals Total}$. Y is the score that is used, in conjunction with the true cheating status of each case, by a receiver operating characteristic curve to discriminate cheaters from non-cheaters. The $\beta_i$ coefficients are the regression weights used to multiply by the scores of the various variables in the equation.

Cheating Algorithm Part 2—Impaired Cheaters Versus Normal Cheaters: A 70% random sub-sample of the 847 applicants classified, by in-person testing, as impaired cheaters or normal cheaters were analyzed using stepwise logistic regression to look for variables discriminating impaired cheaters from normal cheaters. A similar set of candidate variables from the memory test and demographic variables were submitted for inclusion into the stepwise logistic regression. From this analysis, variables that were clearly non-predictors were excluded from the model. Bootstrap analysis was then performed using one thousand random samples of equal numbers of impaired and non-impaired cheaters—forty three to fifty five per group—and logistic regression was performed with each random sample to generate a bootstrapped confidence interval for each variable. Variables whose coefficient values had confidence intervals that included zero were excluded from the model. The remaining variables in the model were run through a second iteration of this process so that they had to survive stepwise regression followed by bootstrapped confidence interval estimation to remain in the final model for part 2. To validate the resulting final model for part 2, the full set of fifty seven impaired cheaters were selected, and a 9% random sample of the normal cheaters were selected and then classified using a nonparametric ROC curve. This process was repeated twenty five times to obtain the overall accuracy and confidence interval for part 2.

Variables that performed well in part 2 of the cheating classification algorithm were age, gender, education, the number of words recall on the third learning trial, and the number of words recalled on the delayed free recall of animals. Additional parameters that properly weighted the classification algorithm of impaired cheater versus non-impaired cheater included the prior probabilities of cheating by impaired and non-impaired applicants for long-term care policies in the absence of other knowledge.

The algorithm for discriminating impaired versus non-impaired cheaters who had taken the cognitive test by telephone and were classified as a possible cheater was as follows: $Y = -1 \, \ln[\beta_0 *(\text{prevalence of non-impaired cheater/prevalence of impaired cheater})] + \beta_1 *\text{age} + \beta_2 *\text{gender} + \beta_3 *\text{education} + \beta_4 *\text{Trial 3 Total} + \beta_5 *\text{Delayed Free Recall of Animals Total}$. Y is the score that is used, in conjunction with the true status of each case, by a receiver operating characteristic curve to discriminate impaired cheaters from non-impaired cheaters. The $\beta_i$ coefficients are the regression weights used to multiply by the scores of the various variables in the equation.

Figure 3B:
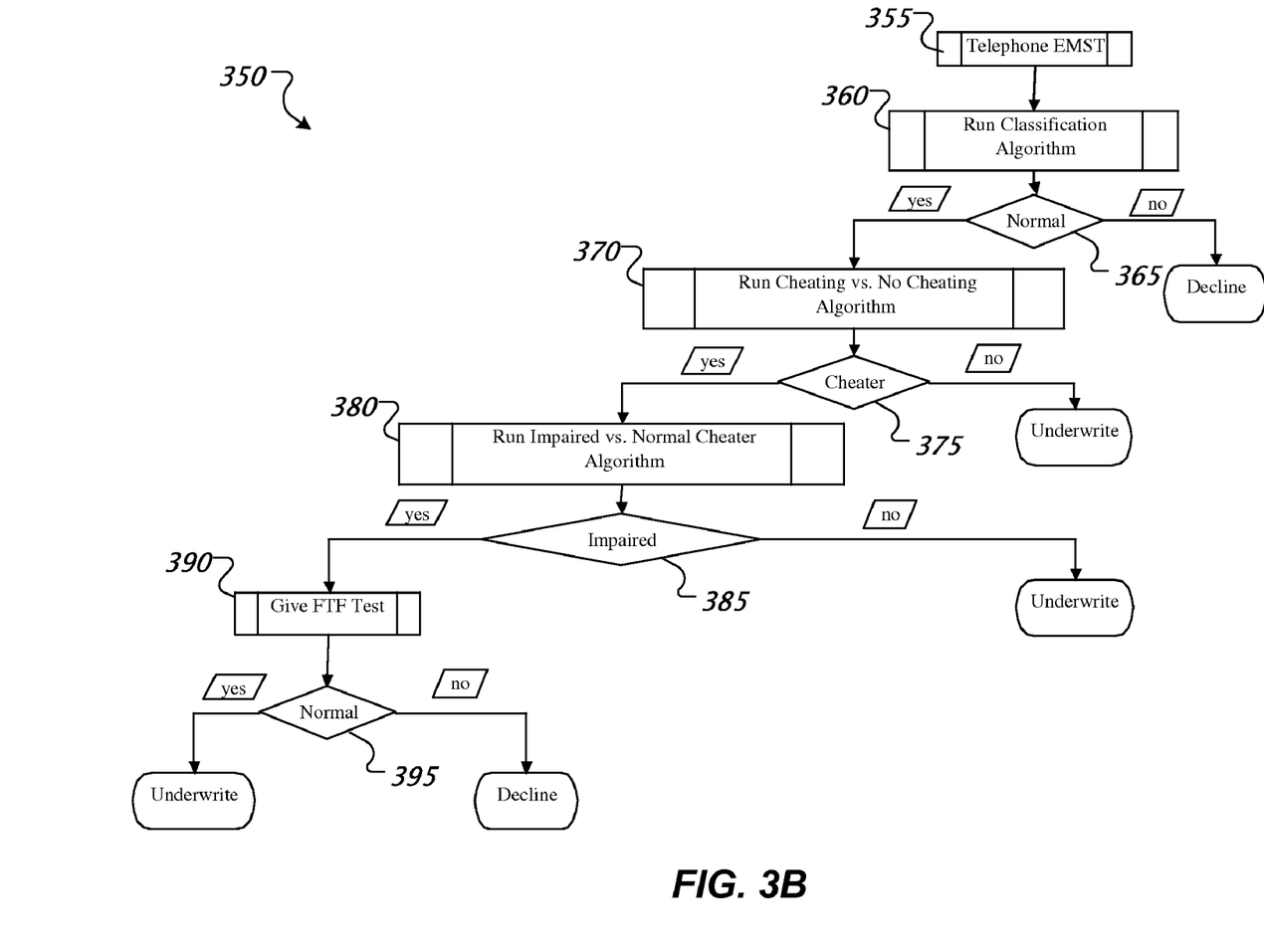
FIG. 3B shows an exemplary process of detecting cheating on telephone administered cognitive testing of a long-term care insurance applicant.

Such classification algorithm(s) can thus be used to detect cheating by a long-term care insurance applicant taking a cognitive test over the telephone. FIG. 3B shows an exemplary process 350 of detecting cheating on telephone administered cognitive testing of a long-term care insurance applicant. Telephone based EMST (Enhanced Mental Skills Test) testing can be performed (355). Classification algorithm(s) can be run (360) using results of the testing. A check can then be made (365) to determine whether to decline coverage, or proceed further.

If a normal determination is made (365), cheating versus no-cheating algorithm(s) can be run (370). A check can then be made (375) to assess whether cheating has occurred. If not, the potential underwriting of an insurance policy can be triggered. If cheating has likely occurred, the process can proceed further where impaired versus normal-cheater algorithm(s) can be run (380). A check can then be made (385) to assess whether a likely cheater is a likely impaired cheater. If not, the potential underwriting of an insurance policy can be triggered. If the likely cheater is likely an impaired cheater, a face to face (FTF) or other validation test can be given (390). A check can then be made (395) to assess impairment and either decline coverage or potentially trigger the underwriting of an insurance policy.

A total of 18.9% of the 15,038 applicants were either reported cheaters (14.4%) or suspected cheaters (4.5%). Of the 30% sub-sample of 847 reported and suspected cheaters re-tested in-person, 94% and 6% of them were classified as normal cheaters and impaired cheaters, respectively. Compared to the 2.6% prevalence of impairment among persons not suspected of cheating, cheaters are 2.3 times more likely to be impaired than non-cheaters.

Table 2 below summarizes the savings in claims costs for the sample of 15,038 applicants who were screened normally by telephone and were evaluated for cheating using a subset of multiple versions of the classification algorithm. The different versions correspond to different cut points on the ROC curve used. The second and last columns of the table are normalized to allow generalization of the findings to any sample size.

TABLE 2

Range of Costs and Cost Savings for Different Algorithm Versions

| Algorithm Version | Additional Cost Per Normal Tel Test to Detect Impaired Cheaters | Current Claims ($201,500 per claim) Among All Telephone Normal Applicants Without Cheating Algorithm | Claims Saved By Detecting Tel Normal Impaired Cheaters ($201,500 per claim) | Net Claims Savings Due to Detecting Tel Normal Impaired Cheaters | Net Claims Savings Per 1,000 Telephone Normal Applicants |
|---|---|---|---|---|---|
| V1_11.2_13.1 | $(5.25) | $(59,808,475) | $20,292,161 | $20,213,161 | $1,344,139 |
| V2_11.2_13.1 | $(6.64) | $(59,808,475) | $24,564,195 | $24,464,320 | $1,626,833 |
| V3_11.2_13.1 | $(7.85) | $(59,808,475) | $24,564,195 | $24,446,195 | $1,625,628 |
| V4_11.2_13.1 | $(8.73) | $(59,808,475) | $27,768,221 | $27,636,971 | $1,837,809 |
| V10_11.2_13.1 | $(15.14) | $(59,808,475) | $39,516,314 | $39,288,689 | $2,612,627 |
| V13_11.2_13.1 | $(16.21) | $(59,808,475) | $39,516,314 | $39,272,564 | $2,611,555 |
| V21_11.2_13.1 | $(20.20) | $(59,808,475) | $41,652,331 | $41,348,581 | $2,749,606 |
| V20_11.2_13.1 | $(23.74) | $(59,808,475) | $42,720,339 | $42,363,339 | $2,817,086 |
| V19_11.2_13.1 | $(26.46) | $(59,808,475) | $43,788,348 | $43,390,473 | $2,885,389 |
| V18_11.2_13.1 | $(39.87) | $(59,808,475) | $50,196,399 | $49,596,899 | $3,298,105 |

Table 3 shows the classification performance statistics of parts 1 and 2 of the cheating algorithm when used together to classify the 15,038 subjects into impaired cheaters versus everyone else (normal cheaters and non-cheaters who passed the test when given by telephone). The sensitivity is the accuracy of detecting impaired cheaters and the specificity is the accuracy of detecting everyone else. To determine sensitivity, the sub-sample of 847 cheaters was used.

TABLE 3

Classification Performance Statistics for Different Algorithm Versions

| Algorithm Version | Sn | Sp | Acc | PPV | NPV |
|---|---|---|---|---|---|
| V1_11.2_13.1 | 34% | 91% | 87% | 6.8% | 98.6% |
| V2_11.2_13.1 | 41% | 88% | 85% | 6.6% | 98.7% |
| V3_11.2_13.1 | 41% | 86% | 84% | 5.7% | 98.6% |
| V4_11.2_13.1 | 46% | 88% | 85% | 7.2% | 98.8% |
| V10_11.2_13.1 | 66% | 83% | 82% | 7.3% | 99.2% |
| V13_11.2_13.1 | 66% | 81% | 80% | 6.6% | 99.2% |
| V21_11.2_13.1 | 70% | 79% | 79% | 6.3% | 99.2% |
| V20_11.2_13.1 | 71% | 78% | 78% | 6.2% | 99.3% |
| V19_11.2_13.1 | 73% | 77% | 77% | 6.0% | 99.3% |
| V18_11.2_13.1 | 84% | 64% | 65% | 4.4% | 99.5% |

The results show that there is a trade-off between sensitivity and specificity, such that one cannot have both high sensitivity and specificity. Considering the two tables together, there are greater savings in future claims costs when one selects algorithms with a higher Negative Predictive Value, which means that fewer impaired cheaters were misclassified. The tradeoff for this greater future claims savings is a higher cost of paying for repeat testing in-person, which can go from a low of $5.25 per normal telephone test for the algorithm with the smallest future claims savings, to a high of $39.87 per normal telephone test for the algorithm with the greatest future claims savings.

Parts 1 and 2 of the Cheating Algorithm described above can be improved by an analysis of the order of words recalled in each trial for impaired cheaters versus normal cheaters. Thus, analyzing a person's responses on a cognitive test, with respect to responses of a group of people, using a classification algorithm can also involve evaluating a probability of an order of items recalled by the person given probabilities of recall patterns for the group of people. The recall patterns (across trials) for an individual can be compared with known recall patterns for a group of people whose brain conditions are already established to a desired level of accuracy. Given this information for the group of people, a good estimate of the conditional probability of recalling a particular set of items in a particular order can be determined for impaired versus non-impaired individuals and for impaired cheaters versus non-impaired cheaters. This information can be compared with an individual's recall pattern(s) to determine whether or not the current individual likely cheated on the cognitive test.

The information for the group of people can be a set of well-classified cases generated in the following manner. A relatively large population of subjects can be evaluated with an extensive neuropsychological test battery, with functional measures, with severity staging measures (the Clinical Dementia Rating Scale, the Functional Assessment Staging Test, and/or other measures), with laboratory testing and brain imaging. The evaluated population is "relatively large" in the sense that there are enough cases to provide statistically significant results in light of the number of modeled categories, e.g., over four hundred subjects when the number of tuple categories (discussed further below) is sixteen. The evaluated population should include normal subjects and subjects who are known to have cheated on a given cognitive test.

Correspondence analysis can be used to analyze the cognitive test results for the subjects (e.g., the binary score vectors of the training sample), and to compute the optimal row score matrix, optimal column score matrix and the singular value matrix. Correspondence analysis is an analytical method that has been largely used in quantitative anthropology and the social sciences. Its primary function is to maximize the canonical correlation between the rows and columns of an input data matrix so that the maximum amount of information in the data can be explained. Mathematically, it is designed to provide the best linear solution to the explanation of the information (variance) in the data.

In some embodiments, correspondence analysis can be used to maximize the explanation of the information that distinguishes impaired cheaters versus non-impaired cheaters. In the case of the CWL, the information consists of the patterns of recalled plus non-recalled words in each trial. In this sense, subject scores generated by correspondence analysis represent a complex combination of the subject characteristics (both normative and non-normative) plus word list test performance metrics (e.g., words recalled, order recalled, retention time, etc.). The maximization of the explainable information can be accomplished through a singular value decomposition of the input data matrix.

Correspondence analysis reduces the dimensionality of a raw data matrix while minimizing the loss of information. Tschebychev orthogonal polynomials can be used to convert the raw data matrix into an optimal row score matrix, an optimal column score matrix, and a singular value matrix of eigenvalues. These matrices can have the following statistical properties: (1) each row of the optimal row score matrix consists of a vector whose components are multivariate, normally distributed and statistically independent of each other; (2) the optimal row score vectors are also directly comparable because the effects of their marginal totals have been removed; (3) each column of the optimal column score matrix consists of a vector whose components are multivariate, normally distributed and statistically independent; (4) the optimal column score vectors are also directly comparable because the effects of their marginal totals have been removed; (5) the singular value matrix consists of a vector along the diagonal of the matrix, in which each value represents a canonical correlation between the row and column variables of the optimal score matrices. Each value of the vector is statistically independent of the other values, and indicates the magnitude of the contribution of each component of the optimal row and column score vectors; the rank of these three matrices defines the number of statistically independent components needed to account for all of the explainable variance (non-noise) in the raw data. The rank is usually of much lower dimension than the number of rows or columns. This means that the transformation of the input data matrix into a set of statistically orthogonal matrices (via singular value decomposition) can yield a massive reduction in dimensionality while continuing to account for most of the explainable information in the input data.

Thus, the optimal row scores represent the pattern of both recalled and not recalled words in each trial after removing the effect of the total number of words recalled, and the optimal column scores represent the effects of recalling or not recalling a given word in a given trial after removing the effect of the sample distribution. In this regard, the optimal row and optimal column scores are not simple weightings of the number of words recalled, their difficulty, their order or their position in the wordlist, or the specific sample used. Rather, the optimal row and column scores provide the best linear solution to explaining the total variance (information) of the raw data.

Correspondence analysis can thus produce optimal row and column score vectors that only require a relatively small number of components (the first two or three components in many cases) to characterize the majority of the explainable variance of the input data matrix. These optimal row and column score vectors can be derived by the simultaneous and inseparable use of the information from both normative and non-normative cases as well as recalled and non-recalled words per trial to maximize data reduction and explanation of the total variance. The optimal column score and singular value matrices can be used for classification of future subjects, while the optimal row score matrix can be used to develop a statistical classification algorithm, such as one using logistic regression or discriminant analysis.

Various different cognitive tests and cognitive function scoring techniques can be used. In any event, the cognitive test data can be analyzed to identify a person as a likely cheater (230). The identification can be a Boolean indication or a number, such as a measure of probability. The identification can be output to a device in various manners, including displaying or printing a cheating indication to an output device, transmitting the cheating indication over a network to a computer system, or saving the cheating indication in a computer-readable medium for use as input to further assessment programs.

As noted above, analyzing a person's responses on a cognitive test, with respect to responses of a group of people, can involve evaluating a probability of an order of items recalled by the person given probabilities of recall patterns for the group of people. The items learned and tested need not be words. However, the present disclosure focuses on the case of the items being words, in the context of the CWL. This is done for purposes of clarity in this disclosure and in no way limits the application of the systems and techniques described to these specific examples. In general, the described systems and techniques can be used in any cognitive test in which the pattern of recall of an item across testing trials can be measured. Moreover, the described systems and techniques can allow for variations in: (1) the number of learning trials; (2) the number of testing trials; (3) the types of learning trials used (e.g., presenting items visually or audibly, verifying or not verifying that the subject correctly registered or understood the item presented, providing cues for items not recalled, learning trials in which the subject is presented only items not recalled in the previous learning trial); (4) the types of testing trials (e.g., delayed cued recall versus delayed recognition versus delayed free recall, delayed free recall plus providing cues for items not recalled); (5) the number of items in the test list; (6) the number of items presented from the test list in each learning trial; and (7) the types of items presented in the test list (e.g., items presented as words, pictures or other visual displays, sounds, smells, tastes, and items presented by touching them).

A recall pattern can be determined for each of multiple items across the recall trials. For example, subject test performance can be captured in the following form; let:

$$d_{ijk} = \begin{cases} 1 & \text{if individual } i \text{ responds correctly to item } j \text{ on trial } k \\ 0 & \text{if individual } i \text{ responds incorrectly to item } j \text{ on trial } k \end{cases}$$

Then, the basic scoring element for the subject can be the response vector:

$$z_{ij} = (d_{ij1}, d_{ij2}, \ldots, d_{ijK})$$

where K is the total number of trials. There are $2^K$ possible response tuples for each word. For the CERAD Wordlist, there are 16 ($2^4$) response tuples for each list word. Each of the $2^K$ possible response tuples per word is assigned a unique response tuple value, c, which, for a given subject's recall of that word across K trials is:

$$c = \sum_{k=1}^{K} (2^k d_{ijk})$$

Given a response tuple, c, the data can be coded as follows:

$$x_{ijc} \equiv \begin{cases} 1 & \text{if } c \text{ is the item } j \text{ response tuple for subject } i \\ 0 & \text{Otherwise} \end{cases}$$

As will be appreciated, this approach allows the response tuple value, c, to be used as a binary address within a computer system to access $x_{ijc}$, thus enabling more efficient processing. In any event, the goal can then be to identify response tuples that optimize discrimination between impaired cheaters and non-impaired cheaters.

Many different types of classification algorithms can be applied to such data, including correspondence analysis, ordinal logistic regression, Bayesian hierarchical methods, and classification and regression trees. The example detailed below is based on discriminant analysis.

A probability of the recall patterns for the person can be evaluated, given probabilities of the recall patterns for the group of people. For example, suppose that for a given population, each word has a fixed set of probabilities of falling into the $2^K$ response tuples. Namely, for a given word, j, the prior probability response tuple vector, $p_{jc}$, of all possible response tuples is:

$$P(x_{ijc}=1)=p_j \rightarrow \text{Multinomial}(1;p_{j1},p_{j2},\ldots,p_{jC}).$$

Note that $p_j$ is the prior probability response tuple vector that would be assigned to any subject for the given word, j, until more information is known (such as the subject's performance for word j). Next, let the set consisting of the prior probability response tuple vectors for all list words be defined as the prior probability response tuple profile, p, which equals $<p_{1c}, p_{2c}, \ldots, p_{Jc}>_{c=1}^{C}$. The implicit presumption here is that each word's probability of recall is independent of the other list words, which is why the words in a learning list should have low associability.

When a subject has performed the specified number of trials, K, one can then compute their posterior probability response tuple profile, which is:

$$P(D_i \mid p) = \prod_{j=1}^{M} \prod_{c=1}^{C} p_j^{x_{ijc}}$$

$D_i = <x_{ijc}>_{j=1}^{M}$, represents the ith subject's response tuple for each of the M list words, and $p_j$ is the jth probability response tuple vector for list word j across the K selected trials. Note that the term, $x_{ijc}$, equals 1 only for the response tuples, $p_{jc}$, that characterize the recall performance of the given subject, i, across the list words.

The group membership of subject i (e.g., impaired cheater versus non-impaired cheater) can be defined by an indicator variable, $\alpha_i$, where:

$$a_i = \begin{cases} 1 & \text{if subject } i \text{ is impaired cheater} \\ 0 & \text{if subject } i \text{ is non-impaired cheater} \end{cases}$$

Bayes theorem can be used to classify the subject to a particular group by evaluating the probability of their response tuple profiles given the probabilities of their response tuples:

$$P(a_i = 1 \mid D_i) = \frac{P(a=1)P(D_i \mid a=1)}{P(a=1)P(D_i \mid a=1) + P(a=0)P(D_i \mid a=0)} \quad (1)$$

Where $P(\alpha_i=1)$ and $P(\alpha_i=0)$ can be interpreted as the prior probability of membership to impaired cheater and non-impaired cheater groups respectively. In equation (1), the reliability of classifying a given subject into the proper group depends upon the accuracy of the estimates of the response tuples, c, that are most relevant to group discrimination. If there is a sufficiently large data set where the group membership, $\alpha$, is known, then the estimated probability of belonging to a given group, $\alpha$ (e.g., impaired cheater versus non-impaired cheater), for a given response tuple, c, and a given word, j, can be given by:

$$\hat{p}_{jca} = \frac{\sum_{i=1}^{N} a_i(x_{ijc} = c)}{N} \quad (2)$$

for a=0, 1 groups; i=1, ..., N subjects; c=1, 2, ..., $2^K$ response tuples; j=1, 2, ... M words. Note that the term $\alpha_i(x_{ijc}=c)$ is set equal to "1" for all subjects belonging to the group being estimated. The group being estimated is made up of those individuals whose recall pattern of the word, j, corresponds to the unique response tuple specified by the value, c, across the specified set of K trials.

Since the number of response tuples for any given word increases exponentially with the number of trials, large samples may be needed to obtain reliable estimates of the response tuple profiles, p, particularly if some of the response tuples, c, are uncommon. For the CWL, there are four interesting combinations of trials that provide a useful dissection of memory performance. The first three immediate free recall trials provide response tuples that measure working memory performance in the prefrontal cortex. The delayed free recall trial response tuples provide a measure of hippocampal storage and retrieval combined. The delayed recognition trial response tuples provide a measure of hippocampal storage. The first four trials or all five trials combined provide overall measures of memory performance.

For the four-trial CWL response tuples, one needs thousands of cases to obtain adequate estimates of each possible response tuple for each word. A database of cases can be built for this purpose, in which group membership is not explicitly known but can be reasonably accurately estimated by a previously established, validated algorithm (see e.g., Cho, et al., "Early Detection and Diagnosis of MCI Using the MCI Screen Test," The Japanese Journal of Clinical and Experimental Medicine, 2007; 84(8):1152-1160; Trenkle, et al., "Detecting Cognitive Impairment in Primary Care: Performance Assessment of Three Screening Instruments," Journal of Alzheimer's Disease, 2007; 11(3):323-335; and Shankle et al., "Method to improve the detection of mild cognitive impairment", PNAS, Vol. 102, No. 13, pp. 4919-4924, 2005).

Group membership of each case in the database can be independently determined twice by the algorithm, first using a high sensitivity cut-point (e.g., Sn=96%, Sp=88%), which can identify a relatively pure sample of non-impaired cheaters, and then using a high specificity cut-point (e.g., Sn=83%, Sp=98%), which can identify a relatively pure sample of impaired cheaters. The performance of the group membership probability estimates derived from equation (2) can then be evaluated by each of these two cut-points for each response tuple of each word. This evaluation can be accomplished using each set of probability estimates independently to classify a different sample of subjects with known group membership. Note that an implicit presumption of this method is that the classification error attributable to the previously established algorithm is random relative to the response tuples.

Figure 4:
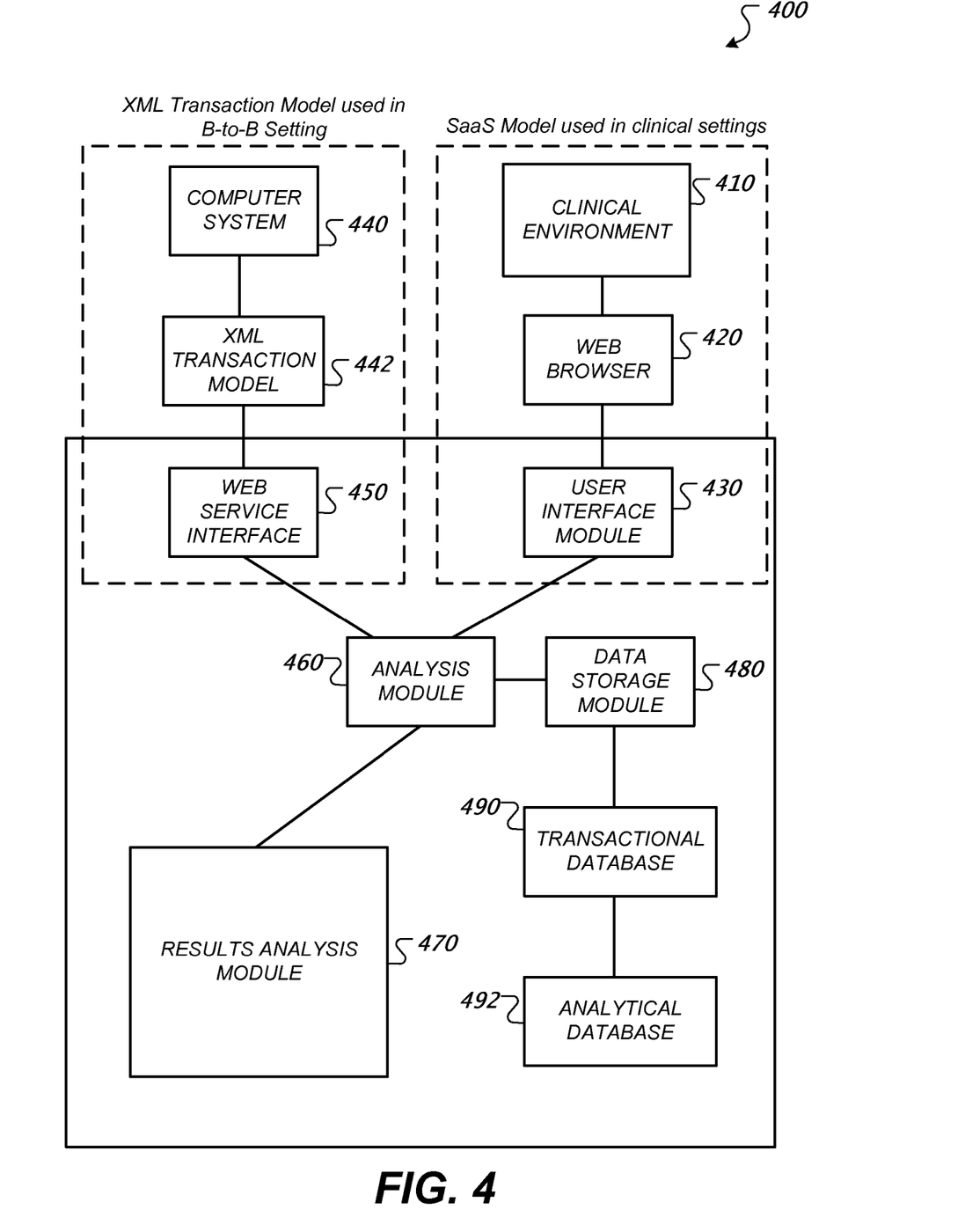
FIG. 4 shows another exemplary system used to identify cheaters on a cognitive test.

FIG. 4 shows another exemplary system 400 used to identify cheaters on a cognitive test. The exemplary system described can perform a variety of functions including data analysis, storage and viewing, and remote access and storage capabilities useful for analyzing results of a cognitive test, including identifying cheaters on the cognitive test, such as described elsewhere in this specification.

A Software as a Service (SaaS) model can provide network based access to the software used to identify cheaters on a cognitive test. This central management of the software can provide advantages, which are well known in the art, such as offloading maintenance and disaster recovery to the provider. A user, for example, a test administrator within a clinical environment 410, can access test administration software within the test administration system via a web browser 420. A user interface module 430 receives and responds to the test administrator interaction.

In addition, a customer's computer system 440 can access software and interact with the test administration system using an eXtensible Markup Language (XML) transactional model 442. The XML framework provides a method for two parties to send and receive information using a standards-based, but extensible, data communication model. A web service interface 450 receives and responds to the customer computer system 440 in XML format. For example, an XML transactional model can be useful for storage and retrieval of the structured data relating to the cognitive test.

An analysis module 460 analyses inputs from the web service interface 450 and the user face module 430, and produces test results to send. The analysis module uses a results analysis module 470 to perform the test analysis to identifying cheaters. The results analysis module 470 can, for example, incorporate the methods described elsewhere in this specification.

A data storage module 480 transforms the test data collected by the user interface module 430, web service interface 450, and the resulting data generated by the analysis module 460 for permanent storage. A transactional database 490 stores data transformed and generated by the data storage module 480. For example, the transactional database can keep track of individual writes to a database, leaving a record of transactions and providing the ability to roll back the database to a previous version in the event of an error condition. An analytical database 492 can store data transformed and generated by the data storage module 480 for data mining and analytical purposes.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer-readable medium. The propagated signal is an artificially generated signal, e.g., a machine-generated electrical, optical, or electromagnetic signal that is generated to encode information for transmission to suitable receiver apparatus for execution by a computer. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a cross-platform runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results. The actions recited in the claims can be performed using different statistical classification procedures, such as discriminant analysis, stepwise multivariate regression or general linear models, rather than logistic regression as described above. The actions recited in the claims can be performed using different orthogonal transformations of the raw input data, such as principal components analysis, multi-dimensional scaling, or latent variable analysis, rather than correspondence analysis as described above.

Moreover, additional techniques can be employed in combination with those described above. Cheaters from non-cheaters can be distinguished based on additional checks for similarities in the pattern of performance. Statistical techniques can be used to detect strange patterns in the data. Some examples include techniques to detect outliers, order effects, abnormal dispersion, and spurious correlations. Use of such techniques in combination with the system and techniques described above employs the premise that it is difficult to invent naturalistic data, particularly those with multiple dimensions.

What is claimed is:

1. A computer-implemented method comprising:
receiving first information concerning a person, the first information specifying the person's responses, and lack thereof, for items of a cognitive test administered to the person, wherein the cognitive test comprises multiple item-recall trials used to assess cognitive impairment;
analyzing the first information using a classification algorithm trained on second information concerning a group of people to whom the cognitive test has been administered, the classification algorithm generated in accordance with a first part and a second part, the first part distinguishing between cheaters and non-cheaters, and the second part distinguishing between impaired cheaters and non-impaired cheaters; and
identifying, based on the analyzing, the person as a cheater requiring a verification test to confirm an initial result of the cognitive test.

2. The method of claim 1, wherein the classification algorithm is configured to check for cheating strategies characteristic of persons with Alzheimer's disease or a related disorder (ADRD).

3. The method of claim 1, wherein the classification algorithm is selected to maximize sensitivity while minimizing reduction in specificity, which preserves a high negative predictive value while maintaining a low misclassification rate for impaired cheaters, and the group of people comprising a first sample and a second sample, the method further comprising:
analyzing data in the first part for the first sample to identify a subset of variables that discriminate between cheaters and non-cheaters, and validating results in the first part using the second sample; and
analyzing, in the second part, data of persons identified as cheaters in the first part to identify a subset of variables that discriminate between impaired cheaters and non-impaired cheaters.

4. The method of claim 3, wherein the subset of variables that discriminate between cheaters and non-cheaters comprises education and multiple numbers corresponding to items recalled on two or more of the multiple item-recall trials including a delayed free recall trial, and the subset of variables that discriminate between impaired cheaters and non-impaired cheaters comprises age, gender, education and a number corresponding to items recalled on at least one of the multiple item-recall trials.

5. The method of claim 1, wherein the multiple item-recall trials comprise word recall tests of memory, and the analyzing comprises distinguishing between impaired and non-impaired individuals based on a total number of words recalled across the trials.

6. The method of claim 1, wherein the analyzing comprises evaluating a probability of an order of items recalled by the person given probabilities of recall patterns for the group of people.

7. A non-transitory computer-readable medium encoding a computer program product operable to cause data processing apparatus to perform operations comprising:
receiving first information concerning a person, the first information specifying the person's responses, and lack thereof, for items of a cognitive test administered to the person, wherein the cognitive test comprises multiple item-recall trials used to assess cognitive impairment;
analyzing the first information using a classification algorithm trained on second information concerning a group of people to whom the cognitive test has been administered, the classification algorithm generated in accordance with a first part and a second part, the first part distinguishing between cheaters and non-cheaters, and the second part distinguishing between impaired cheaters and non-impaired cheaters; and
identifying, based on the analyzing, the person as a cheater requiring a verification test to confirm an initial result of the cognitive test.

8. The non-transitory computer-readable medium of claim 7, wherein the classification algorithm is configured to check for cheating strategies characteristic of persons with Alzheimer's disease or a related disorder (ADRD).

9. The non-transitory computer-readable medium of claim 7, wherein the classification algorithm is selected to maximize sensitivity while minimizing reduction in specificity, which preserves a high negative predictive value while maintaining a low misclassification rate for impaired cheaters, and the group of people comprising a first sample and a second sample, the operations further comprising:
analyzing data in the first part for the first sample to identify a subset of variables that discriminate between cheaters and non-cheaters, and validating results in the first part using the second sample; and
analyzing, in the second part, data of persons identified as cheaters in the first part to identify a subset of variables that discriminate between impaired cheaters and non-impaired cheaters.

10. The non-transitory computer-readable medium of claim 9, wherein the subset of variables that discriminate between cheaters and non-cheaters comprises education and multiple numbers corresponding to items recalled on two or more of the multiple item-recall trials including a delayed free recall trial, and the subset of variables that discriminate between impaired cheaters and non-impaired cheaters comprises age, gender, education and a number corresponding to items recalled on at least one of the multiple item-recall trials.

11. The non-transitory computer-readable medium of claim 7, wherein the multiple item-recall trials comprise word recall tests of memory, and the analyzing comprises distinguishing between impaired and non-impaired individuals based on a total number of words recalled across the trials.

12. The non-transitory computer-readable medium of claim 7, wherein the analyzing comprises evaluating a probability of an order of items recalled by the person given probabilities of recall patterns for the group of people.

13. A system comprising:
a user device; and
one or more computers operable to interact with the device and to perform operations comprising:
receiving first information concerning a person, the first information specifying the person's responses, and lack thereof, for items of a cognitive test administered to the person, wherein the cognitive test comprises multiple item-recall trials used to assess cognitive impairment;
analyzing the first information using a classification algorithm trained on second information concerning a group of people to whom the cognitive test has been administered, the classification algorithm generated in accordance with a first part and a second part, the first part distinguishing between cheaters and non-cheaters, and the second part distinguishing between impaired cheaters and non-impaired cheaters; and
identifying, based on the analyzing, the person as a cheater requiring a verification test to confirm an initial result of the cognitive test.

14. The system of claim 13, wherein the classification algorithm is configured to check for cheating strategies characteristic of persons with Alzheimer's disease or a related disorder (ADRD).

15. The system of claim 13, wherein the classification algorithm is selected to maximize sensitivity while minimizing reduction in specificity, which preserves a high negative predictive value while maintaining a low misclassification rate for impaired cheaters, and the group of people comprising a first sample and a second sample, the operations further comprising:
   analyzing data in the first part for the first sample to identify a subset of variables that discriminate between cheaters and non-cheaters, and validating results in the first part using the second sample; and
   analyzing, in the second part, data of persons identified as cheaters in the first part to identify a subset of variables that discriminate between impaired cheaters and non-impaired cheaters.

16. The system of claim 15, wherein the subset of variables that discriminate between cheaters and non-cheaters comprises education and multiple numbers corresponding to items recalled on two or more of the multiple item-recall trials including a delayed free recall trial, and the subset of variables that discriminate between impaired cheaters and non-impaired cheaters comprises age, gender, education and a number corresponding to items recalled on at least one of the multiple item-recall trials.

17. The system of claim 13, wherein the multiple item-recall trials comprise word recall tests of memory, and the analyzing comprises distinguishing between impaired and non-impaired individuals based on a total number of words recalled across the trials.

18. The system of claim 13, wherein the analyzing comprises evaluating a probability of an order of items recalled by the person given probabilities of recall patterns for the group of people.

19. The system of claim 13, wherein the one or more computers comprise a server system operable to interact with the device through a data communication network, and the device is operable to interact with the server as a client.

20. The system of claim 13, wherein the device comprises a user interface device, the one or more computers comprise the user interface device, and the operations further comprise outputting an indication of the identified person to a device comprising a computer-readable medium.

* * * * *